(12) United States Patent
Betley et al.

(10) Patent No.: US 8,551,994 B2
(45) Date of Patent: Oct. 8, 2013

(54) AFFINITY ADSORBENTS FOR FIBRINOGEN

(75) Inventors: Jason Richard Betley, Buntingford (GB); James Christopher Pearson, Cambridge (GB); Ben Martin Beacom, Cambridge (GB); Tadeusz Antoni Podgorski, Cambridge (GB); Robert William Pannell, Cambridge (GB)

(73) Assignee: Prometic Biosciences Ltd (IM)

( * ) Notice: Subject to any disclaimer, the term of this patent is extended or adjusted under 35 U.S.C. 154(b) by 845 days.

(21) Appl. No.: 11/913,528

(22) PCT Filed: May 9, 2006

(86) PCT No.: PCT/GB2006/001695
§ 371 (c)(1),
(2), (4) Date: Aug. 24, 2009

(87) PCT Pub. No.: WO2006/120429
PCT Pub. Date: Nov. 16, 2006

(65) Prior Publication Data
US 2009/0326201 A1 Dec. 31, 2009

(30) Foreign Application Priority Data
May 9, 2005 (GB) .................................. 0509442.0

(51) Int. Cl.
*A01N 43/66* (2006.01)
*C07K 16/06* (2006.01)
*C12Q 1/56* (2006.01)

(52) U.S. Cl.
USPC .............. 514/246; 514/242; 530/382; 435/13

(58) Field of Classification Search
None
See application file for complete search history.

(56) References Cited

U.S. PATENT DOCUMENTS

| 3,879,388 | A | * | 4/1975 | Varsanyi et al. | ............... 544/196 |
| 6,037,457 | A | | 3/2000 | Lord | |
| 6,117,996 | A | | 9/2000 | Lowe et al. | |
| 2005/0238641 | A1 | | 10/2005 | Burton et al. | |

FOREIGN PATENT DOCUMENTS

| WO | WO 00/67900 A | 11/2000 |
| WO | WO-2004/052870 | * 6/2004 |

OTHER PUBLICATIONS

Burton, N. P. et al., "Design of novel affinity adsorbents for the purification of trypsin-like proteases," *Journal of Molecular Recognition*, Heyden & Son Ltd., London, GB, 1992, vol. 5, pp. 55-68.

Lowe, C. R., "Combinatorial approaches to affinity chromatography," *Current Opinion in Chemical Biology*, 2001, vol. 5, pp. 248-256.

* cited by examiner

*Primary Examiner* — Satyanarayana R Gudibande
(74) *Attorney, Agent, or Firm* — Saliwanchik, Lloyd & Eisenschenk

(57) ABSTRACT

For the separation, removal, isolation, purification, characterization, identification or quantification of fibrinogen or a protein that is a fibrinogen analogue, an affinity adsorbent is used that is a compound of formula II wherein one X is N and the other is N, C—Cl or C—CN; Y is O, S or $NR_2$; O Z is O, S or $NR_3$; $R_2$ and $R_3$ are each H, alkyl, hydroxyalkyl, benzyl or β-phenylethyl; n is 0 to 6; A is a support matrix, optionally linked to the triazine ring by a spacer; $R_7$ is a group bearing a positive charge at neutral pH; W is an optional linker; V is an aromatic group; and $R_8$ and $R_9$ are each H, OH, alkyl, alkoxy, amino, $NH_2$, acyloxy, acylamino, $CO_2H$, sulphonic acid, carbamoyl, sulphamoyl, alkylsulphonyl or halogen or a cyclic structure such as a morpholino group, or $R_8$ and $R_9$ are linked to form such a cyclic structure.

7 Claims, No Drawings

AFFINITY ADSORBENTS FOR FIBRINOGEN

This application is a National Stage Application of International Application Number PCT/GB2006/001695, filed May 9, 2006; which claims priority to Great Britain Application No. 0509442.0, filed May 9, 2005.

FIELD OF THE INVENTION

This invention relates to compounds and their use as affinity ligands.

BACKGROUND TO THE INVENTION

Fibrinogen is a dimeric protein, each half of which is composed of disulfide-bonded polypeptide chains designated Aα, Bβ and γ. In the liver, the genes for the Aα- and Bβ-chains encode single products of 610 and 461 amino acid residues, respectively. In contrast, alternative splicing of transcripts of the γ-chain gene yield γ-chain variants of slightly different lengths (411 and 427 residues), the shorter of which constitutes ~90% of the final product. The predominant form of fibrinogen is secreted into the circulation with a molecular mass of ~340 kDa. Following its secretion from the liver, the protein exists not only in plasma, but also in lymph and interstitial fluid. In healthy individuals, the concentration of fibrinogen in plasma is between 4 and 10 μM. Importantly, that concentration can increase by as much as much as 400% during times of physiological stress.

Fibrinogen is converted to fibrin by thrombin, a trypsin-like serine proteinase. Thrombin hydrolyzes at least two specific Arg-Gly bonds within fibrinogen. This process leads initially to the formation of fibrin protofibrils which can associate laterally, forming thicker fibres that, in turn, can associate to form even thicker and branched fibrin bundles. Such bundles are further stabilised by cross-links formed between Lys and Gln residues located within the α-chains of neighboring fibrin molecules, to form a 3-D meshwork capable of preventing or limiting blood flow. This process of cross-linking is catalysed by the enzyme Factor XIIIa.

Two types of congenital abnormalities of fibrinogen exist, afibrinogenemia and dysfibrinogenemia. Afibrinogenemia is a quantitative deficiency that results in bleeding diatheses. The term hypofibrinogenemia refers to a less severe fibrinogen deficiency. Dysfibrinogenemia is marked by functional abnormalities of fibrinogen that may result in either bleeding or thrombosis. Patients may be treated with fibrinogen concentrate or cryoprecipitate. Fibrinogen is also commonly used during surgery as an adjunct to hemostasis in the form of fibrin sealants. These are typically two-component systems comprising fibrinogen (e.g. in the form of fibrinogen concentrate) and thrombin in appropriate pharmaceutical compositions.

A concern in the administration of these partially purified forms of fibrinogen is the presence of contaminating proteins. An affinity-based purification method for the isolation of fibrinogen would therefore be useful. Such a purification method would be especially useful if it were able to isolate fibrinogen from non-depleted plasma, in a specific fashion, leaving all other protein components intact for further manipulation.

WO97/10887 discloses triazine-based compounds, useful as affinity adsorbents, of formula I

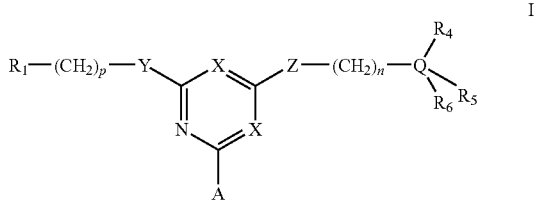

wherein $R_1$ is H, alkyl, hydroxyalkyl, cyclohexyl, $NH_2$, phenyl, naphthyl, 1-phenylpyrazole, indazole, benzthiazole, benzoxazole or benzimidazole, any of which aromatic groups can be substituted with one or more of alkyl, alkoxy, acyloxy, acylamino, amino, $NH_2$, OH, $CO_2H$, sulphonyl, carbamoyl, sulphamoyl, alkylsulphonyl and halogen;
one X is N and the other is N, C—Cl or C—CN;
Y is O, S or $NR_2$;
Z is O, S or $NR_3$;
$R_2$ and $R_3$ are each H, alkyl, hydroxyalkyl, benzyl or (5-phenylethyl;
Q is benzene, naphthalene, benzthiazole, benzoxazole, 1-phenylpyrazole, indazole or benzimidazole;
$R_4$, $R_5$ and $R_6$ are each H, OH, alkyl, alkoxy, amino, $NH_2$, acyloxy, acylamino, $CO_2H$, sulphonic acid, carbamoyl, sulphamoyl, alkylsulphonyl or halogen;
n is 0 to 6;
p is 0 to 20; and
A is a support matrix, optionally linked to the triazine ring by a spacer.

Compounds of formula I are disclosed as having affinity for proteins such as immunoglobulins, insulin, Factor VII or human growth hormone.

Compounds of related structure are disclosed in WO00/67900 and WO03/097112. They have affinity for endotoxins.

SUMMARY OF THE INVENTION

Surprisingly, it has been found that certain compounds, many of which are novel, are useful for affinity-based isolation of fibrinogen. These compounds are of formula II

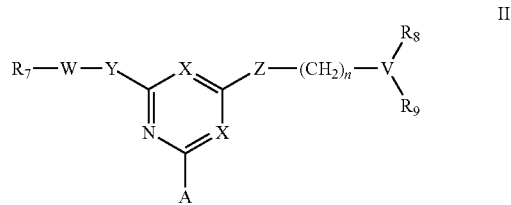

wherein X, Y, Z, n and A are as defined for formula I above;
$R_7$ is a group bearing a positive charge at neutral pH;
W is an optional linker;
V is as described above for Q, but alternatively may be a nodal structure; and
$R_8$ and $R_9$ are as defined for $R_4$, $R_5$ and $R_6$, but additionally include cyclic structures, or $R_8$ and $R_9$ are linked to form such a cyclic structure.

Further, compounds of the invention include the corresponding ligands, in which A is replaced by a functional group, linked directly or indirectly to the triazine ring, which can be immobilised on a support matrix. The terms "ligand" and "adsorbent" may be used interchangeably, below.

DESCRIPTION OF THE INVENTION

WO97/10887, WO00/67900 and WO03/097112 disclose how combinatorial libraries of ligands can be built on a solid support. Their disclosures, including examples of embodiments and procedures common to the present invention, are incorporated herein by reference. During the screening of a set of these combinatorial libraries with pooled human plasma as feedstock, a number of ligands were identified as being capable of selectively binding and eluting human fibrinogen.

Compounds of formula II, for use in the invention, can be prepared by procedures known to those skilled in the art. Such procedures are described in the 3 PCT publications identified above; they can be readily adapted to the preparation of new compounds.

WO97/10887 gives examples of A, including spacers or linkers L via which the triazine ring may be linked to a solid support M. As described in WO97/10887, such supports include agarose, silica, cellulose, dextran, starch, alginate, carrageenan, synthetic polymers, glass and metal oxides. Such materials may be activated before reaction to form an adsorbent of this invention.

L may be, for example, -T-(-$V^1$—$V^2$)$_m$—, wherein

T is O, S or —$NR^7$—;

m is 0 or 1;

$V^1$ is an optionally substituted hydrocarbon radical of 2 to 20 C atoms; and $V^2$ is O, S, —COO, —CONH—, —NHCO—, —$PO_3H$—, —NH-arylene-$SO_2$—$CH_2$—$CH_2$— or —$NR_8$—; and $R^7$ and $R^8$ are each independently H or $C_{1-6}$ alkyl.

In compounds of the invention, $R_7$ is a group bearing a positive charge at neutral pH. Examples of such groups are guanidino, amidino etc. or derived from an amino acid such as alanine or phenylalanine.

W (if present) is an optional linker which may be an alkyl, cycloalkyl, oxyalkyl or aromatic ring structure, optionally substituted (e.g. with a carboxylic acid as in arginine or other).

V is as described above for Q, but alternatively may be a nodal structure. Examples of such structures include a simple tertiary amine or methine function, to permit the formation of, for example, a morpholino group.

$R_8$ and $R_9$ are as defined for $R_4$, $R_5$ and $R_6$, but additionally include cyclic structures, or $R_8$ and $R_9$ are linked to form such a cyclic structure. Examples of such cyclic structures include carbocyclic and heterocyclic rings, saturated, unsaturated or aromatic, typically containing 4 to 8 ring atoms of which 1, 2 or 3 are individually selected from N (or NH), O or S; an example is morpholine.

In a preferred embodiment of the invention, the fibrinogen-binding ligand or adsorbent is of formula III (which will be protonated at physiological pH)

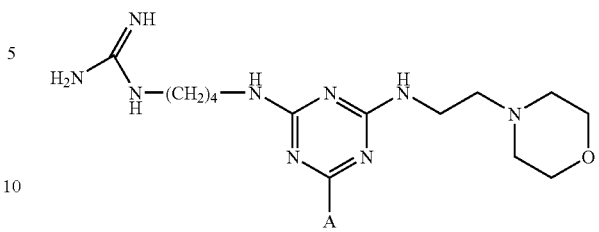

In another preferred embodiment of the invention, the fibrinogen-binding ligand or adsorbent is of formula IV

IV

In yet another preferred embodiment of the invention, the fibrinogen-binding ligand or adsorbent is represented by structure V

V

In a further preferred embodiment of the invention, the fibrinogen-binding ligand or adsorbent is represented by structure VI

VI

In a most preferred embodiment of the invention, the fibrinogen-binding ligand or adsorbent is represented by structure VII

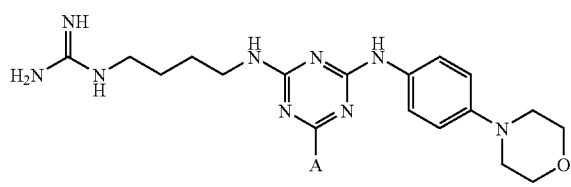

VII

The fibrinogen-binding ligands and adsorbents described herein are useful for the purification of fibrinogen from complex mixtures including, but not limited to, human plasma and recombinant fermentation supernatants. This utility is demonstrated below in Example 7, by chromatography experiments using human pooled plasma.

The term "fibrinogen" is used herein to describe fibrinogen itself and also analogues that have the functional characteristics of fibrinogen, e.g. in terms of affinity to a given compound described herein. Thus, the analyte may be a protein that is a functional fragment of fibrinogen, or a structural analogue having one, more of all of the same binding sites, or a fusion protein.

The following Examples illustrate the invention.

Example 1

Synthesis of 4-(4-morpholino)anilinyl dichlorotriazine

Cyanuric chloride (16.1 g) was dissolved in tetrahydrofuran (130 mL) and cooled to 0° C. in an ice/salt bath. 4-(4-Morpholino)aniline (29.61 g) in THF (400 mL) was added to the solution of cyanuric chloride at such a rate that the temperature did not exceed 0° C. After addition was complete, the mixture was stirred at 0° C. for a further 30 minutes, before the solution was added to a mixture of ice (700 g) and water (1.5 L). The resulting solid was filtered off, washed with water (1 L), before being dried in a vacuum oven at 45° C. to constant weight (28.54 g).

Example 2

Synthesis of Adsorbent III

6% cross-linked Purabead agarose gel (1000 g settled in Reverse Osmosis (RO) water) was slurried with RO water (667 mL), 10 M sodium hydroxide (NaOH) (90 mL), and epichlorohydrin (127 mL). The slurry was stirred over 2 hours. After a sample was taken for analysis, the slurry was filtered, then washed with RO water (12×1 L). Analysis for epoxy groups showed that the gel was derivatised with 19.2 μmol epoxy groups per g of settled gel.

The gel was drained before RO water (400 mL) and 0.88 specific gravity aqueous ammonia solution (100 mL) were added. The mixture was stirred and heated to 40° C., then stirred at this temperature over 16 hours. After a sample was taken for analysis, the slurry was filtered, then washed with RO water (12×500 mL). TNBS analysis for amine groups showed that the gel was derivatised with 28.0 μmol amine groups per g of settled gel.

The settled, aminated gel (500 g) was suspended in 1 M potassium phosphate pH 7.0 (500 mL), then allowed to drain. To this gel were then added 1 M potassium phosphate pH 7.0 (125 mL) and RO water (125 mL). The slurry was stirred vigorously while acetone (250 mL) was added. After cooling in an ice/salt bath over 30 minutes, cyanuric chloride (12.5 g) in cold acetone (125 mL) was added in one portion. The mixture was stirred at 0° C. over 1 hour, before being washed with 50% aqueous acetone (5×500 mL), RO water (5×500 mL), 50% aqueous acetone (5×500 mL), and RO water (10× 500 mL). The gel was allowed to settle under gravity, before a sample was taken for analysis. Analysis for chloride release indicated that the gel was derivatised with 26.1 μmol substituted dichlorotriazine per g of settled gel.

Settled gel from the previous stage (238 g) was slurried with RO water (138 mL) under ice/salt cooling, before 2-(4-morpholino)ethylamine (4.39 g) in cold (8° C.) RO water (95 mL) was added, such that the reaction temperature did not exceed 8° C. The mixture was then stirred at 8° C. over 1 hour. After a sample was taken for analysis, the slurry was filtered, then washed with RO water (10×250 mL). Analysis for chloride release indicated that the gel was derivatised with 23.8 μmol substituted monochlorotriazine per g of settled gel.

To 238 g (settled) of the gel was added agmatine sulfate (15.42 g) dissolved in RO water (200 mL-pH adjusted to pH 10, then made up to a final volume of 238 mL with RO water). The mixture was stirred at 60° C. overnight, while maintaining the pH at 10. After a sample of the supernatant was taken for analysis, the slurry was filtered, then washed with RO water (15×250 mL). Analysis for chloride release indicated that the gel had been derivatised with 17.0 μmol agmatine per g of settled gel.

The gel was incubated in a final concentration of 0.5 M NaOH/25% v/v aqueous ethanol overnight at 40° C., then washed with 0.5 M NaOH/25% v/v aqueous ethanol (5×250 mL). After the final wash was allowed to drain under gravity, 0.5 M NaOH/25% v/v aqueous ethanol (250 mL) was added and the mixture incubated at 40° C. overnight. The gel was then washed with 0.5 M NaOH/25% ethanol (5×250 mL), then RO water (10×250 mL). The gel was then incubated in a final concentration of 0.5 M NaOH overnight at 40° C., then washed with 0.5 M NaOH (5×250 mL). After the final wash was allowed to drain under gravity, 0.5 M NaOH (250 mL) was added and the mixture incubated at 40° C. overnight. The gel was then washed with 0.5 M NaOH (5×250 mL), then RO water (10×250 mL). After washing with 0.1 M PBS pH 7.0 (3×250 mL), the gel was washed a further time with RO water (10×250 mL), before storage in the cold room at 4° C. in 20% v/v aqueous ethanol.

Example 3

Synthesis of Adsorbent IV

6% cross-linked Purabead agarose gel (650 g settled in RO water) was slurried with RO water (438 mL), 10 M sodium hydroxide (NaOH) (59 mL), and epichlorohydrin (83 mL). The slurry was stirred over 2 hours. After a sample was taken for analysis, the slurry was filtered then washed with 12×1 L RO water. Analysis for epoxy groups showed that the gel was derivatised with 16.5 μmol epoxy groups per g of settled gel.

The gel was drained, before RO water (520 mL) and 0.88 specific gravity ammonia solution (130 mL) were added. The mixture was stirred and heated to 40° C., then stirred at this temperature over 16 hours. After a sample was taken for analysis, the slurry was filtered, then washed with RO water (12×1 L). TNBS analysis for amine groups showed that the gel was derivatised with 22.9 μmol amine groups per g of settled gel.

A 500 g portion of the settled, aminated gel was slurried with DMF (500 mL) then allowed to drain. This gel was then slurried with DMF (250 mL), and diisopropylethylamine (DI- PEA) (11.0 mL) added with stirring. The mixture was stirred over 10 minutes, then 4-(4-morpholino)anilinyl dichlorotriazine (20.6 g) in DMF (250 mL) added in one portion. The mixture was stirred at room temperature over 3 hours. After a sample was taken for analysis, the slurry was filtered, then washed with 70% v/v aqueous DMF (4×150 mL), 50% DMF (2×150 mL), and RO water (10×150 mL). Analysis for chloride release indicated that the gel was derivatised with 20.2 μmol substituted monochlorotriazine per g of settled gel. Residual amine was undetectable by TNBS assay after derivatisation.

A 150 g (settled) portion of the gel was slurried in 1 M sodium borate buffer (150 mL) and the pH adjusted to 10 with 10 M sodium hydroxide. Arginine (5.50 g) was added in one portion. The mixture was stirred at 60° C. overnight, while maintaining the pH at 10. After a sample of the supernatant was taken for analysis, the slurry was filtered then washed with RO water (12×150 mL). Analysis for chloride release indicated that the gel had been derivatised with 22.4 μmol arginine per g of settled gel.

The gel was incubated in a final concentration of 0.5 M NaOH/25% v/v aqueous ethanol overnight at 40° C., then washed with 0.5 M NaOH/25% v/v aqueous ethanol (5×150 mL). After the final wash was allowed to drain under gravity, 0.5 M NaOH/25% v/v aqueous ethanol (150 mL) was added and the mixture incubated at 40° C. overnight. The gel was then washed with 0.5 M NaOH/25% ethanol (5×150 mL), then RO water (10×150 mL). The gel was then incubated in a final concentration of 0.5 M NaOH overnight at 40° C., then washed with 0.5 M NaOH (5×150 mL). After the final wash was allowed to drain under gravity, 0.5 M NaOH (150 mL) was added and the mixture incubated at 40° C. overnight. The gel was then washed with 0.5 M NaOH (5×150 mL), then RO water (10×150 mL). After washing with 0.1 M PBS pH 7.0 (3×150 mL), the gel was washed a further time with RO water (10×150 mL), before storage in the cold room in 20% v/v aqueous ethanol.

Example 4

Synthesis of Adsorbent V

6% cross-linked Purabead agarose gel (650 g settled in RO water) was slurried with RO water (438 mL), 10 M sodium hydroxide (NaOH) (59 mL), and epichlorohydrin (83 mL). The slurry was stirred over 2 hours. After a sample was taken for analysis, the slurry was filtered, then washed with RO water (12×1 L). Analysis for epoxy groups showed that the gel was derivatised with 16.5 μmol epoxy groups per g of settled gel.

The gel was drained before RO water (520 mL) and 0.88 specific gravity aqueous ammonia solution (130 mL) were added. The mixture was stirred and heated to 40° C., then stirred at this temperature over 16 hours. After a sample was taken for analysis, the slurry was filtered then washed with RO water (12×1 L). TNBS analysis for amine groups showed that the gel was derivatised with 22.9 μmol amine groups per g of settled gel.

A 500 g portion of the settled, aminated gel was slurried with DMF (500 mL), then allowed to drain. This gel was then slurried with DMF (250 mL), and DIPEA (11.0 mL) added with stirring. The mixture was stirred over 10 minutes, then 4-(4-morpholino)anilinyl dichlorotriazine (20.6 g) in DMF (250 mL) added in one portion. The mixture was stirred at room temperature over 3 hours. After a sample was taken for analysis, the slurry was filtered then washed with 70% v/v aqueous DMF (4×150 mL), 50% v/v aqueous DMF (2×150 mL), and RO water (10×150 mL). Analysis for chloride release indicated that the gel was derivatised with 20.2 μmol substituted monochlorotriazine per g of settled gel. Residual amine was undetectable by TNBS assay after derivatisation.

A 150 g (settled) portion of the gel was slurried in 1 M sodium borate buffer (150 mL) and the pH adjusted to 10 with 10 M sodium hydroxide. Arginine amide dihydrochloride (7.75 g) was added in one portion. The mixture was stirred at 60° C. overnight, while maintaining the pH at 10. The slurry was filtered, then washed with RO water (15×150 mL). Analysis for residual chloride of the washed and settled gel indicated that the gel had been derivatised to completion by arginine amide.

The gel was incubated in a final concentration of 0.5 M NaOH/25% v/v aqueous ethanol overnight at 40° C., then washed with 0.5 M NaOH/25% v/v aqueous ethanol (5×150 mL). After the final wash was allowed to drain under gravity, 0.5 M NaOH/25% v/v aqueous ethanol (150 mL) was added and the mixture incubated at 40° C. overnight. The gel was then washed with 0.5 M NaOH/25% v/v aqueous ethanol (5×150 mL), then RO water (10×150 mL). The gel was then incubated in a final concentration of 0.5 M NaOH overnight at 40° C., then washed with 0.5 M NaOH (5×150 mL). After the final wash was allowed to drain under gravity, 0.5 M NaOH (150 mL) was added and the mixture incubated at 40° C. overnight. The gel was then washed with 0.5 M NaOH (5×150 mL), then RO water (10×150 mL). After washing with 0.1 M PBS pH 7.0 (3×150 mL), the gel was washed a further time with RO water (10×150 mL), before storage in the cold room in 20% v/v aqueous ethanol.

Example 5

Synthesis of Adsorbent VI

6% cross-linked Purabead agarose gel (650 g settled in RO water) was slurried with RO water (438 mL), 10 M sodium hydroxide (NaOH) (59 mL), and epichlorohydrin (83 mL). The slurry was stirred over 2 hours. After a sample was taken for analysis, the slurry was filtered then washed with RO water (12×1 L). Analysis for epoxy groups showed that the gel was derivatised with 16.5 μmol epoxy groups per g of settled gel.

The gel was drained before RO water (520 mL) and 0.88 specific gravity ammonia solution (130 mL) were added. The mixture was stirred and heated to 40° C., then stirred at this temperature over 16 hours. After a sample was taken for analysis, the slurry was filtered then washed with 12×1 L RO water (12×1 L). TNBS analysis for amine groups showed that the gel was derivatised with 22.9 μmol amine groups per g of settled gel.

Settled aminated gel (70 g) was slurried in 1 M potassium phosphate (70 mL) and allowed to settle. 1 M potassium phosphate (20 mL) was then added, the mixture stirred vigorously, and acetone (10 mL) added. The mixture was cooled to 0° C. in an ice salt bath, before cyanuric chloride (1.75 g) in cold acetone (17.5 mL) was added in one portion. The slurry was stirred over 1 hour at 0-4° C., before being drained, then washed with 50% v/v aqueous acetone (5×70 mL), RO water (5×70 mL), with 50% v/v aqueous acetone (5×70 mL), and RO water (10×70 mL). Analysis revealed the attachment of 18.0 μmol dichlorotriazine groups per g of settled gel.

The dichlorotriazinyl agarose (55 g) was washed with 50% v/v aqueous DMF, then slurried in 50% v/v aqueous DMF (55 mL). 4-(4-Morpholino)aniline (1.23 g) was dissolved in 75% v/v aqueous DMF (15 mL) and cooled on ice, prior to addition to the dichlorotriazinyl agarose. The mixture was reacted at 4°

C. over 60 mins. A sample of supernatant was taken after this time, before the gel was washed with 50% DMF (5×100 mL) and RO water (10×100 mL). Analysis of chloride ion released in the reaction indicated a loading of the amine of 20 6 µmol per g of settled gel.

A 37 g (settled) portion of the gel was slurried in 1 M sodium borate buffer (37 mL) and the pH adjusted to 9 with 10 M sodium hydroxide. 4-Aminobenzamidine dihydrochloride (1.93 g) was added in one portion. The mixture was stirred at 60° C. overnight, while maintaining the pH at 10. The slurry was filtered, then washed with RO water (15×150 mL). The gel was washed with RO water (10×150 mL), before storage in the cold room at 4° C. in 20% v/v aqueous ethanol.

Example 6

Synthesis of Adsorbent VII

6% cross-linked Purabead agarose gel (650 g settled in RO water) was slurried with RO water (438 mL), 10 M sodium hydroxide (NaOH) (59 mL), and epichlorohydrin (83 mL). The slurry was stirred over 2 hours. After a sample was taken for analysis, the slurry was filtered then washed with RO water (12×1 L). Analysis for epoxy groups showed that the gel was derivatised with 16.5 µmol epoxy groups per g of settled gel.

The gel was drained before RO water (520 mL) and 0.88 specific gravity ammonia solution (130 mL) were added. The mixture was stirred and heated to 40° C., then stirred at this temperature over 16 hours. After a sample was taken for analysis, the slurry was filtered then washed with RO water (12×1 L). TNBS analysis for amine groups showed that the gel was derivatised with 22.9 µmol amine groups per g of settled gel.

A 150 g portion of the settled, aminated gel was slurried with DMF (150 mL) then allowed to drain. This gel was then slurried with DMF (75 mL), and DIPEA (1.38 mL) added with stirring. The mixture was stirred over 10 minutes, then 4-(4-morpholino)anilinyl dichlorotriazine (2.58 g) in DMF (75 mL) added in one portion. The mixture was stirred at room temperature over 3 hours. After a sample was taken for analysis, the slurry was filtered then washed with 70% v/v aqueous DMF (4×150 mL), 50% v/v aqueous DMF (2×150 mL), and RO water (12×150 mL). Analysis for chloride release indicated that the gel was derivatised with 21.4 µmol substituted monochlorotriazine per g of settled gel. Residual amine analysis indicated that 0.8 µmol amine groups per g of settled gel remained after derivatisation.

A 132 g (settled) portion of the gel was slurried in 1 M sodium borate buffer (132 mL) and the pH adjusted to 10 with 10 M sodium hydroxide. Agmatine sulfate (3.73 g) was added in one portion. The mixture was stirred at 60° C. overnight, while maintaining the pH at 10. After a sample of the supernatant was taken for analysis, the slurry was filtered, then washed with RO water (15×150 mL). Analysis for chloride release indicated that the gel had been derivatised with 19.9 µmol agmatine per g of settled gel.

The gel was incubated in a final concentration of 0.5 M NaOH/25% v/v aqueous ethanol overnight at 40° C., then washed with 0.5 M NaOH/25% v/v aqueous ethanol (5×150 mL). After the final wash was allowed to drain under gravity, 0.5 M NaOH/25% v/v aqueous ethanol (150 mL) was added and the mixture incubated at 40° C. overnight. The gel was then washed with 0.5 M NaOH/25% v/v aqueous ethanol (5×150 mL), then RO water (10×150 mL). The gel was then incubated in a final concentration of 0.5 M NaOH overnight at 40° C., then washed with 0.5 M NaOH (5×150 mL). After the final wash was allowed to drain under gravity, 0.5 M NaOH (150 mL) was added and the mixture incubated at 40° C. overnight. The gel was then washed with 0.5 M NaOH (5×150 mL), then RO water (10×150 mL). After washing with 0.1 M PBS pH 7.0 (3×150 mL), the gel was washed a further time with RO water (10×150 mL), before storage in the cold room at 4° C. in 20% v/v aqueous ethanol.

Example 7

Chromatography on Human Plasma

Chromatography experiments were performed with each of Adsorbents III, IV, V, VI, and VII, using a 1 cm diameter, 10 mL column volume omnifit column using a Biologic LP chromatography system. The column was equilibrated with 5 column volumes of 13 mM sodium citrate, 140 mM sodium chloride pH 7.0 at 100 cm/hr. Human plasma (0.45 µm filtered, 100 mL) was then loaded at 50 cm/hr. Post-load wash was with 13 mM sodium citrate, 140 mM sodium chloride pH 7.0, to baseline absorbance. The column was then eluted with 0.3 M glycine, 0.5 M sodium chloride and 1% w/v sodium cholate pH 9.0, and sanitised with 2 M guanidine hydrochloride pH 7.0. The elution fraction was neutralised immediately with 0.4 M HCl prior to analysis. Load, non-bound, and elution fractions were analysed by nephelometry to determine binding and elution capacities. SDS PAGE was carried out to determine purity.

The purity of fibrinogen in each eluate was greater than 85%. Binding and elution capacities are presented in Table 1.

TABLE 1

| Adsorbent | Binding Capacity (mg/mL) | Elution Capacity (mg/mL) |
|---|---|---|
| III | 3.23 | 3.04 |
| IV | 2.76 | 0.28 |
| V | 6.43 | 3.77 |
| VI | 8.36 | 3.99 |
| VII | 17.97 | 15.04 |

The invention claimed is:

1. A method for purifying fibrinogen or a protein that is a fibrinogen analogue, wherein said method comprises contacting a sample containing fibrinogen or a protein that is a fibrinogen analogue with an affinity adsorbent of formula II:

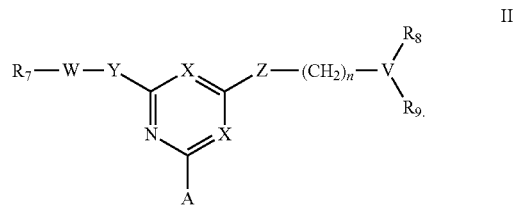

wherein one X is N and the other is N, C—Cl or C—CN;
Y is O, S or $NR_2$;
Z is O, S or $NR_3$;
$R_2$ and $R_3$ are each H, alkyl, hydroxyalkyl, benzyl or β-phenylethyl;
n is 0 to 6;
A is a support matrix selected from agarose, silica, cellulose, dextran, starch, alginate, carrageenan, synthetic polymers, glass and metal oxides, wherein A is optionally linked to the triazine ring by a spacer;

$R_7$ is a group bearing a positive charge at neutral pH;
W is an optional linker; and
either V is an aromatic group, $R^8$ is H, OH, alkyl, alkoxy, amino, acyloxy, acylamino, $CO_2H$, sulphonic acid, carbamoyl, sulphamoyl, alkylsulphonyl or halogen and $R^9$ is a morpholino group, or $VR_8R_9$ is morpholine, wherein the fibrinogen, or the protein that is a fibrinogen analogue, binds to the affinity adsorbent; and wherein said method further comprises recovering the fibrinogen or the protein that is a fibrinogen analogue from the affinity adsorbent, thereby obtaining purified fibrinogen or purified fibrinogen analogue with a purity of greater than 85%.

2. The method, according to claim 1, wherein the adsorbent is of formula III:

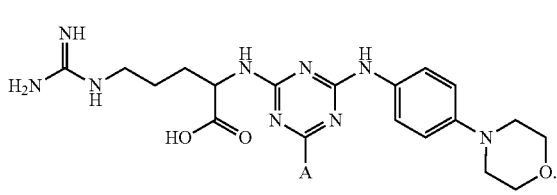

III

3. The method, according to claim 1, wherein the adsorbent is of formula IV:

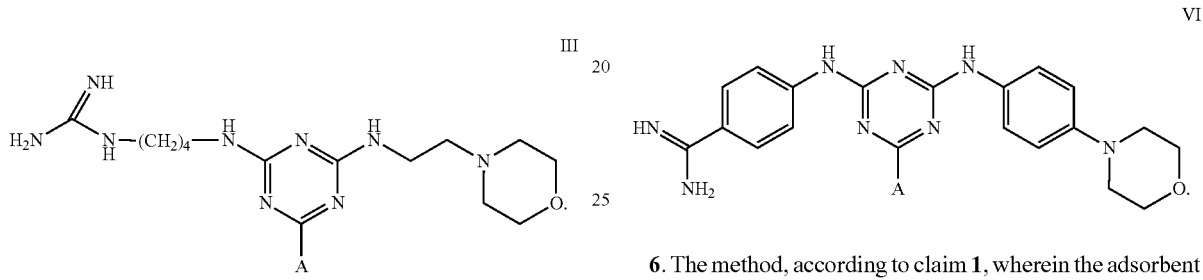

IV

4. The method, according to claim 1, wherein the adsorbent is of formula V:

V

5. The method, according to claim 1, wherein the adsorbent is of formula VI:

VI

6. The method, according to claim 1, wherein the adsorbent is of formula VII:

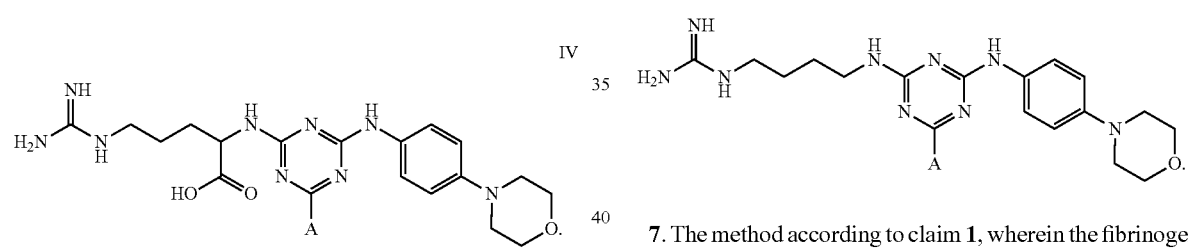

VII

7. The method according to claim 1, wherein the fibrinogen is in a sample of plasma.

* * * * *

UNITED STATES PATENT AND TRADEMARK OFFICE
CERTIFICATE OF CORRECTION

PATENT NO. : 8,551,994 B2  
APPLICATION NO. : 11/913528  
DATED : October 8, 2013  
INVENTOR(S) : Jason Richard Betley et al.

It is certified that error appears in the above-identified patent and that said Letters Patent is hereby corrected as shown below:

In the Claims

Column 12, Lines 9-10,

"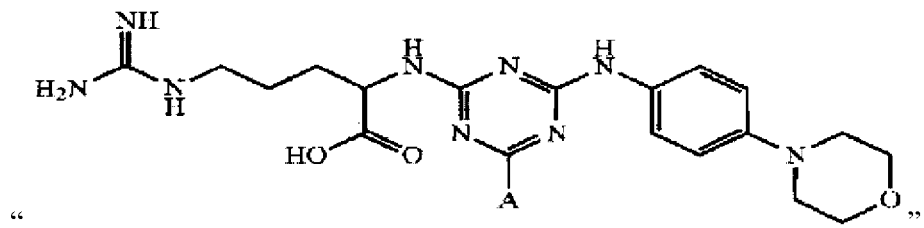"

should read

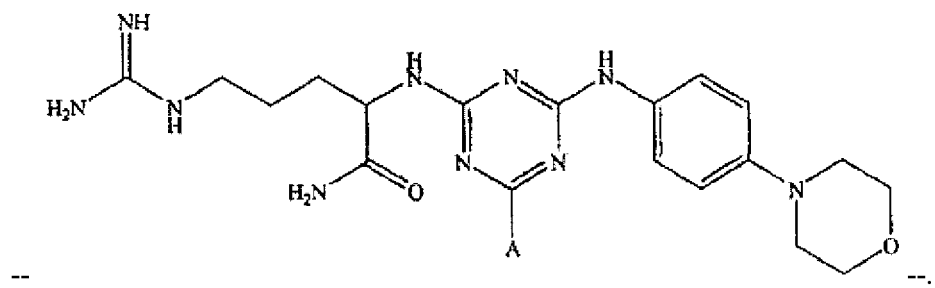

--.

Signed and Sealed this  
Fourth Day of March, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,551,994 B2  Page 1 of 1
APPLICATION NO. : 11/913528
DATED : October 8, 2013
INVENTOR(S) : Betley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1077 days.

Signed and Sealed this

Fifteenth Day of September, 2015

Michelle K. Lee
*Director of the United States Patent and Trademark Office*